(12) United States Patent
North et al.

(10) Patent No.: US 6,960,567 B2
(45) Date of Patent: Nov. 1, 2005

(54) METHOD OF PRODUCING N-[(2S)-SULFANYL-4-(1,5,5-TRIMETHYLHYDANTOINYL)BUTANOYL]-L-LEUCYL-L-TERT-LEUCINE N-METHYLAMIDE AND INTERMEDIATE THEREOF

(75) Inventors: Jeffrey T. North, Manlius, NY (US); Brian Leslie James, East Syracuse, NY (US)

(73) Assignee: Bristol Myers Squibb Company, Princeton, NJ (US)

( * ) Notice: Subject to any disclaimer, the term of this patent is extended or adjusted under 35 U.S.C. 154(b) by 334 days.

(21) Appl. No.: 10/295,652

(22) Filed: Nov. 15, 2002

(65) Prior Publication Data

US 2003/0166506 A1 Sep. 4, 2003

Related U.S. Application Data

(60) Provisional application No. 60/334,912, filed on Nov. 30, 2001.

(51) Int. Cl.$^7$ ............................................. A61K 38/00
(52) U.S. Cl. ........................................................ 514/19
(58) Field of Search ............................................ 514/19

(56) References Cited

U.S. PATENT DOCUMENTS

| 5,981,490 A | * 11/1999 | Baxter et al. .................. 514/19 |
| 6,153,757 A | 11/2000 | Zook et al. |
| 6,262,080 B1 | * 7/2001 | Warshawsky et al. ...... 514/323 |

OTHER PUBLICATIONS

Greene, T.W. et al., "The Role of Protective Groups in Organic Synthesis", $2^{nd}$ Edition, pp. 1–9, (1991).

* cited by examiner

Primary Examiner—Bruce R. Campell
Assistant Examiner—Maury Audet
(74) Attorney, Agent, or Firm—Jacqueline M. Cohen

(57) ABSTRACT

Process for producing N-[(2S)-sulfanyl-4-(1,5,5-trimethylhydantoinyl) butanoyl]-L-leucyl-L-tert-leucine N-methylamide by forming an intermediate compound N-[(2S)-thiobenzoyl-4-(1,5,5-trimethylhydantoinyl) butanoyl]-L-leucyl-L-tert-leucine N-methylamide by an improved process that substantially reduces the presence of contaminants in the reaction mixture.

27 Claims, No Drawings

METHOD OF PRODUCING N-[(2S)-SULFANYL-4-(1,5,5-TRIMETHYLHYDANTOINYL)BUTANOYL]-L-LEUCYL-L-TERT-LEUCINE N-METHYLAMIDE AND INTERMEDIATE THEREOF

This application claims a benefit of priority from U.S. application Ser. No. 60/334,912, filed Nov. 30, 2001, the entire disclosure of which is herein incorporated by reference.

FIELD OF THE INVENTION

The present invention is directed to a process of producing N-[(2S)-sulfanyl-4-(1,5,5-trimethylhydantoinyl)butanoyl]-L-leucyl-L-tert-leucine N-methylamide through a unique process for producing an intermediate thereof N-[(2S)-thiobenzoyl-4-(1,5,5-trimethylhydantoinyl)butanoyl]-L-leucyl-L-tert-leucine N-methylamide in a manner which substantially reduces the presence of contaminants in the reaction mixture.

BACKGROUND OF THE INVENTION

N-[(2S)-sulfanyl-4-(1,5,5-trimethylhydantoinyl)butanoyl]-L-leucyl-L-tert-leucine N-methylamide is a known inhibitor of metalloproteinase and TNF and is therefore believed to be a potent therapeutic strategy for the treatment of inflammatory, infectious, immunological or malignant diseases including, but not limited to, septic shock, haemodynamic shock, sepsis syndrome, post ischarmic reperfusion injury, malaria, mycobacterial infection, meningitis, congestive heart failure, cancer and the like as disclosed in Baxter et al. (U.S. Pat. No. 5,981,490), incorporated herein by reference.

N-[(2S)-sulfanyl-4-(1,5,5-trimethylhydantoinyl)butanoyl]-L-leucyl-L-tert-leucine N-methylamide has been prepared by reacting 1,5,5-trimethyl-3-((3S)-thiobenzoyl-3-carboxypropyl)hydantoin with L-leucyl-L-tert-leucine N-methylamide in the presence of a coupling reagent to produce the intermediate compound N-[(2S)-thiobenzoyl-4-(1,5,5-trimethylhydantoinyl)butanoyl]-L-leucyl-L-tert-leucine N-methylamide which is converted to the desired N-[(2S)-sulfanyl-4-(1,5,5-trimethylhydantoinyl)butanoyl]-L-leucyl-L-tert-leucine N-methylamide. The reaction to form the intermediate compound has been previously conducted in a non-aqueous environment resulting in the formation of the intermediate compound (N-[(2S)-thiobenzoyl-4-(1,5,5-trimethylhydantoinyl)butanoyl]-L-leucyl-L-tert-leucine N-methylamide) as well as undesirable impurities including those indicated below:
N-[(2R)-thiobenzoyl-4-(1,5,5,-trimethylhydantoinyl)butanoyl]-L-leucyl-L-tert-leucine N-methylamide;
Isobutoxycarbonyl-L-leucyl-L-tert-leucine N-methylamide;
2-thiobenzoyl-4-(1,5,5-trimethylhydantoinyl)butanoyl-iso-butanoate; and
2-thiobenzoyl-4-(1,5,5-trimethylhydantoinyl)butanoyl anhydride.

The presence of these impurities reduces the yield of the desired intermediate and increases the cost associated with the production of the end product N-[(2S)-sulfanyl-4-(1,5,5-trimethylhydantoinyl)butanoyl]-L-leucyl-L-tert-leucine N-methylamide.

It would therefore be a significant advance in the art of producing N-[(2S)-sulfanyl-4-(1,5,5-trimethylhydantoinyl)butanoyl]-L-leucyl-L-tert-leucine N-methylamide to provide a process for production which reduces the presence of impurities during production of the intermediate N-[(2S)-thiobenzoyl-4-(1,5,5-trimethylhydantoinyl)butanoyl]-L-leucyl-L-tert-leucine N-methylamide to thereby increase the yield of the intermediate compound as well as the desired N-[(2S)-sulfanyl-4-(1,5,5-trimethylhydantoinyl)butanoyl]-L-leucyl-L-tert-leucine N-methylamide.

SUMMARY OF THE INVENTION

The present invention is directed to the process of producing N-[(2S)-thiobenzoyl-4-(1,5,5-trimethylhydantoinyl)butanoyl]-L-leucyl-L-tert-leucine N-methylamide as an intermediate compound in the production of N-[(2S)-sulfanyl-4-(1,5,5-trimethylhydantoinyl)butanoyl]-L-leucyl-L-tert-leucine N-methylamide. The process of the present invention provides a synthesis in which the presence of contaminants is significantly reduced thereby increasing the yield of the desired intermediate N-[(2S)-thiobenzoyl-4-(1,5,5-trimethylhydantoinyl)butanoyl]-L-leucyl-L-tert-leucine N-methylamide and the final product N-[(2S)-sulfanyl-4-(1,5,5-trimethylhydantoinyl)butanoyl]-L-leucyl-L-tert-leucine N-methylamide.

In accordance with one aspect of the present invention, there is provided a method of producing N-[(2S)-thiobenzoyl-4-(1,5,5-trimethylhydantoinyl)butanoyl]-L-leucyl-L-tert-leucine N-methylamide (I) by reacting 1,5,5-trimethyl-3-((3S)-thiobenzoyl-3-carboxypropyl)hydantoin (II) and L-leucyl-L-tert-leucine N-methylamide (III) with a base, water and an activating agent in the presence of an aprotic solvent. The reaction scheme is shown below in Flow Diagram I.

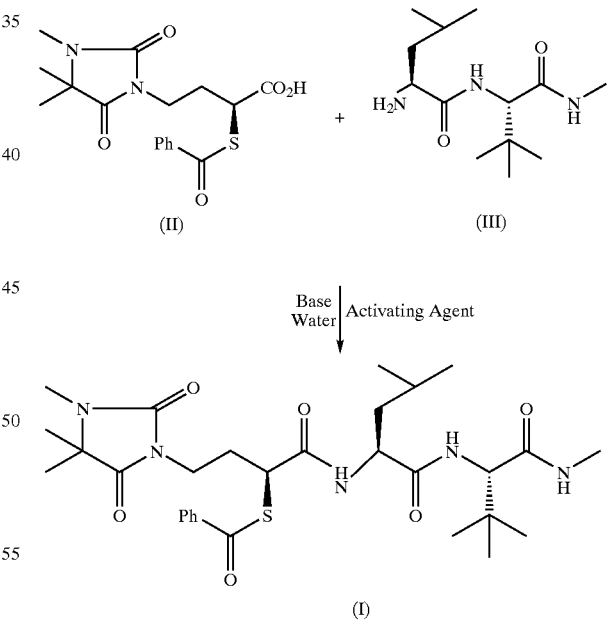

Advantageously, the process of this invention reduces the presence of contaminants including N-[(2R)-thiobenzoyl-4-(1,5,5,-trimethylhydantoinyl)butanoyl]-L-leucyl-L-tert-leucine N-methylamide (IV), Isobutoxycarbonyl-L-leucyl-L-tert-leucine N-methylamide (V), 2-thiobenzoyl-4-(1,5,5-trimethylhydantoinyl)butanoyl-iso-butanoate (VI), and 2-thiobenzoyl-4-(1,5,5-trimethylhydantoinyl)butanoyl anhydride (VII).

(IV)

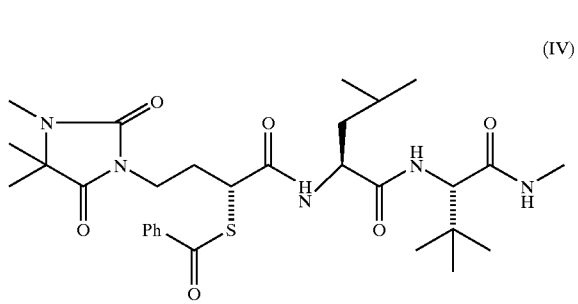

(V)

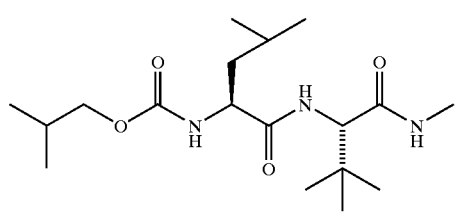

(VI)

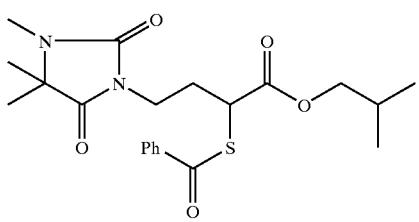

(VII)

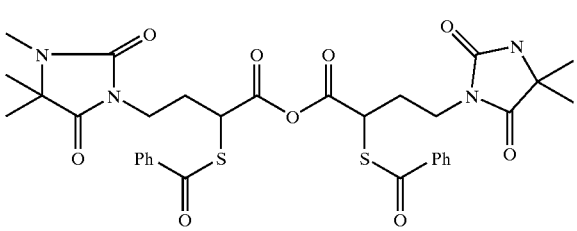

In a further aspect of the present invention, there is provided a method of producing N-[(2S)-sulfanyl-4-(1,5,5-trimethylhydantoinyl)butanoyl]-L-leucyl-L-tert-leucine N-methylamide (VIII) by debenzoylating the intermediate N-[(2S)-thiobenzoyl-4-(1,5,5-trimethylhydantoinyl) butanoyl]-L-leucyl-L-tert-leucine N-methylamide (I). The reaction scheme is shown below in Flow Diagram II.

FLOW DIAGRAM II

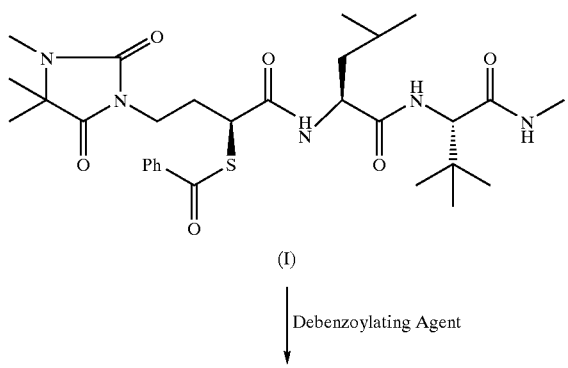

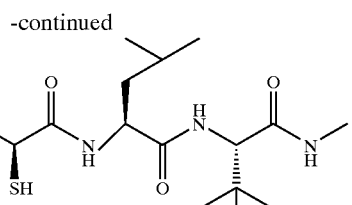

(VIII)

Since the 2S-diastereomer of N-[(2S)-sulfanyl-4-(1,5,5-trimethylhydantoinyl)butanoyl]-L-leucyl-L-tert-leucine N-methylamide is the desired active agent, the starting reactant 1,5,5-trimethyl-3-((3S)-thiobenzoyl-3-carboxypropyl)hydantoin is in the form of the S-enantiomer.

DETAILED DESCRIPTION OF THE INVENTION

The present invention is directed to the production of N-[(2S)-sulfanyl-4-(1,5,5-trimethylhydantoinyl)butanoyl]-L-leucyl-L-tert-leucine N-methylamide through the formation of an intermediate compound N-[(2S)-thiobenzoyl-4-(1,5,5-trimethylhydantoinyl)butanoyl]-L-leucyl-L-tert-leucine N-methylamide which is obtained by the reaction of 1,5,5-trimethyl-3-((3S)-thiobenzoyl-3-carboxypropyl) hydantoin and L-leucyl-L-tert-leucine N-methylamide with a base, water and an activating agent in the presence of an aprotic solvent. Surprisingly, it has been found that the presence of water in the reaction mixture substantially reduces or eliminates typical undesirable by-products including the compounds N-[(2R)-thiobenzoyl-4-(1,5,5-trimethylhydantoinyl)butanoyl]-L-leucyl-L-tert-leucine N-methylamide, isobutoxycarbonyl-L-leucyl-L-tert-leucine-N-methylamide, 2-thiobenzoyl-4-(1,5,5-trimethylhydantoinyl)butanoyl-iso-butanoate, and 2-thiobenzoyl-4-(1,5,5-trimethylhydantoinyl)butanoyl anhydride. The intermediate compound N-[(2S)-thiobenzoyl-4-(1,5,5-trimethylhydantoinyl)butanoyl]-L-leucyl-L-tert-leucine N-methylamide is then debenzolyated to obtain the desired N-[(2S)-sulfanyl-4-(1,5,5-trimethylhydantoinyl)butanoyl]-L-leucyl-L-tert-leucine N-methylamide.

Bases, suitable for use in the processes of the present invention include, but are not limited to, alkali metal hydrides such as sodium hydride and the like; alkaline earth metal hydrides such as calcium hydride and the like; alkali metal hydroxides such as sodium hydroxide, potassium hydroxide and the like; alkaline earth metal hydroxides such as, calcium hydroxide and the like; alkoxides such as sodium methoxide, sodium ethoxide, potassium tert-butoxide and the like, and tertiary amines such as, 4-methylmorpholine, triethylamine, diisopropylethylamine and the like. Preferred bases include tertiary amine bases with 4-methylmorpholine being an especially preferred base.

The activating agents of the present invention are defined herein as agents that react with the carboxylate group of the formula II compound to form reactive intermediate compounds. Activating agents suitable for use in the present invention include, but are not limited to, (1) haloformates including those of formula IX.

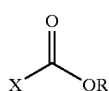

(IX)

Wherein X is Cl, Br or I and R is a $C_1$–$C_6$ alkyl group (branched and unbranched), a $C_3$–$C_7$ cycloakyl group or a substituted or unsubstituted phenyl group; (2) thionyl halides such as thionyl chloride; (3) Vilsmeier reagent (oxalyl chloride/DMF); (4) substituted carbodiimides including $C_1$–$C_6$ alkyl, $C_3$–$C_7$ cycloalkyl and substituted or unsubstituted phenyl carbodiimide with and without the presence of hydroxy benzotriazole; (5) chlorodimethoxytriazine; (6) 4-(4,6-dimethoxy-1,3,5-triazin-2-yl)-4-methylmorpholinium halides (DMTMM); and (7) acid chlorides including $C_1$–$C_6$ alkyl (branched and unbranched) acid chlorides, $C_3$–$C_7$ cycloalkyl acid chlorides and substituted or unsubstituted acid chlorides. Preferred activating agents include haloformates with iso-butylchloroformate being especially preferred.

In a preferred embodiment of the present invention, the activating agent is added to the reaction mixture after the addition of the formula II and III compounds, the base and the water.

Advantageously, the use of water in the present invention reduces the production of undesirable by-products. In a preferred embodiment of the invention, from about 0.1 to 5 molar equivalents, preferably about 1 molar equivalent of water relative to the formula II compound is utilized in the inventive process.

Debenzoylation of the formula I intermediate compound may be performed using standard debenzoylating agents including, but not limited to, alkali metal hydroxides such as sodium hydroxide and the like; alkaline earth metal hydroxides such as calcium hydroxide and the like; alkali metal alkoxides such as sodium methoxide and the like; ammonia; primary amines such as methyl amine and the like; secondary amines such as dimethyl amine and the like; alkali metal thioalkoxides such as sodium thiomethoxide and the like; mineral acids such as HBr and the like; and organic acids such as trifluoroacetic acid and the like. Preferred debenzoylation agents include primary amines with 3-dimethylaminopropylamine being especially preferred. The debenzoylation is preferably conducted in the presence of an aprotic solvent.

Aprotic solvents suitable for use in the preparation of the formula I and VIII compounds of the present invention include, but are not limited to, ethers such as diethyl ether, tetrahydrofuran and the like, esters such as ethyl acetate, isopropyl acetate and the like, aromatic hydrocarbons such as toluene, xylenes and the like, halogenated aromatic hydrocarbons such as chlorobenzene and the like, hydrocarbons such as hexane, heptane and the like, halogenated hydrocarbons such as chloroform, methylene chloride and the like, and nitriles such as acetonitrile. Preferred aprotic solvents include esters. Ethyl acetate is especially preferred for use in the preparation of the formula I compound and isopropyl acetate is especially preferred for use in the preparation of the formula VIII compound.

In a preferred embodiment of the invention, N-[(2S)-sulfanyl-4-(1,5,5-trimethylhydantoinyl) butanoyl]-L-leucyl-L-tert-leucine N-methylamide is produced by first reacting 1,5,5-trimethyl-3-(3S)-thiobenzoyl-3-carboxypropyl) hydantoin and L-leucyl-L-tert-leucine N-methylamide, preferably in about equimolar amounts, with a base (preferably about 1 to 5 molar equivalents, water (preferably about 0.1 to 5 molar equivalents), and an activating agent (preferably about 1 to 2 molar equivalents) in the presence of an aprotic solvent to form the intermediate compound N-[(2S)-thiobenzoyl-4-(1,5,5-trimethylhydantoinyl)butanoyl]-L-leucyl-L-tert-leucine N-methylamide, which is then reacted with a debenzoylating agent.

The formula I intermediate compounds may be isolated by washing and then azeotropically drying the reaction mixture followed by cooling to form a slurry containing N-[(2S)-thiobenzoyl-4-(1,5,5-trimethylhydantoinyl)-butanoyl]-L-leucyl-L-tert-leucine N-methylamide. The thus formed slurry may be filtered followed by washing and drying to obtain N-[(2S)-thiobenzoyl-4-(1,5,5-trimethylhydantoinyl)butanoyl]-L-leucyl-L-tert-leucine N-methylamide as a solid.

In a preferred debenzoylation embodiment of the invention, a deoxygenated slurry containing N-[(2S)-thiobenzoyl-4-(1,5,5,-triethylhydantoinyl) butanoyl]-L-leucyl-L-tert-leucine N-methylamide, dithiothreitol in isopropyl acetate is added to a deoxygenated solution of 3-(dimethylamino) propylamine in methanol. After aqueous work-up, drying and filtering, the desired end product N-[(2S)-sulfanyl-4-(1,5,5-trimethylhydantoinyl) butanoyl]-L-leucyl-L-tert-leucine N-methylamide is obtained.

The final product N-[(2S)-sulfanyl-4-(1,5,5-trimethylhydantoinyl)butanoyl]-L-leucyl-L-tert-leucine N-methylamide can be formulated as a pharmaceutically effective composition for oral administration in the form, for example, as tablets, troches, lozenges, aqueous or oily suspensions, dispersible powders or granules, emulsions, hard or soft capsules, syrups and elixirs and the like. Compositions may also be formulated for administration as suppositories, and for topical use as creams, ointments, jellies, solutions, suspensions and the like as well as mouthwashes and gargles.

Dosage levels of from about 0.05 mg to 140 mg per kilogram of body weight per day are useful for the treatment of the above-mentioned conditions. Further information regarding the preparation of pharmaceutical compositions containing N-[(2S)-sulfanyl-4-(1,5,5-trimethylhydantoinyl) butanoyl]-L-leucyl-L-tert-leucine N-methylamide and their administration to warm blooded animals including humans is disclosed in Baxter et al. (U.S. Pat. No. 5,981,490), incorporated herein by reference.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of N-[(2S)-thiobenzoyl-4-(1,5,5-trimethylhydantoinyl)butanoyl]-L-leucyl-L-tert-leucine N-methylamide 25.0 g of 1,5,5-trimethyl-3-((3S)-thiobenzoyl-3-carboxypropyl)hydantoin and 18.2 g of L-leucyl-L-tert-leucine N-methylamide were added to a reaction vessel. 350 mL of ethyl acetate and 1.2 mL of water were added to the vessel and the contents were agitated. Thereafter, the vessel was cooled to about 10° C. 8.3 mL of 4-methymorpholine was added to the vessel under stirring while maintaining the temperature of the reaction mixture at approximately 10° C.

9.8 mL of iso-butylchloroformate was added to the reaction vessel at a constant rate over approximately 30 minutes. Completion of the reaction after addition of the iso-butylcholoroformate was determined by HPLC analysis.

200 mL of 0.5 N HCl solution was added to the reaction mixture which was warmed to a temperature of between 45 and 55° C. The reaction mixture was agitated for 15 minutes and after agitation, the phases were allowed to separate over the next 15 minutes. The lower, aqueous phase was separated from the upper, product-rich ethyl acetate phase.

The ethyl acetate phase was then combined with 200 mL of 5% aqueous sodium carbonate solution under agitation at a temperature of from 45 to 55° C. Agitation was continued for 15 minutes and the respective phases were allowed to separate over the course of the next 15 minutes. The lower, aqueous phase was again separated from the upper, product-rich ethyl acetate phase.

The product-rich ethyl acetate phase was then combined with 200 mL of deionized water under agitation at a temperature of from 45 to 55° C. followed by separation of the phases over the course of 15 minutes. The lower, aqueous phase was again separated from the upper, product-rich ethyl acetate phase. The ethyl acetate phase was distilled to a volume of about 325 mL (with addition of additional ethyl acetate to maintain volume until the water content was less than 0.5% by Karl Fischer analysis) at a batch temperature of no greater than 85° C. The contents of the reaction vessel were then cooled under agitation to 20–25° C. over about one hour. At this time, 175 mL of heptanes were added at a constant rate to the reaction vessel at 20–25° C. over about 30 minutes. The reaction vessel was cooled under agitation for one hour at 0–5° C.

The reaction mixture was filtered using a Buchner funnel through Whatman No. 1 filter paper to produce a wet cake which was washed with a 40:60 mixture of ethyl acetate-heptanes. The filter cake was then dried under vacuum at about 50°–55° C. for between 2–72 hours at a pressure of about 25–30 inches Hg. N-[(2S)-thiobenzoyl-4-(1,5,5-trimethylhydantoinyl)butanoyl]-L-leucyl-L-tert-leucine N-methylamide was isolated as a solid at a yield of 37.62 g (91%).

EXAMPLE 2

Preparation of N-[(2S)-Sulfanyl-4-(1,5,5-trimethylhydantoinyl)butanoyl]-L-leucyl-L-tert-leucine N-methylamide 15.0 g of N-[(2S)-thiobenzoyl-4-(1,5,5-trimethylhydantoinyl) butanoyl-L-leucyl-L-tert-leucine N-methylamide and 96 mg of dithiothreitol were added to a reaction vessel followed by the addition of 60 mL of deoxygenated isopropyl acetate and 5.58 g of dimethylaminopropyldiamine in 15 mL of deoxygenated methanol. The vessel was heated to about 30° C. for 2–3 hours.

The heated reaction mixture (~96 mL) was combined with 45 mL of deoxygenated 2N HCl and allowed to settle into an aqueous phase (49 mL; pH ~0.5) and a rich organic phase (~71 mL). The aqueous phase containing excess acid was sent to waste.

The rich organic phase was combined with 45 mL of in deoxygenated HCl and allowed to separate wherein the aqueous phase (43 mL; pH ~0.5) was sent to waste. The rich organic phase was then combined with 26 mL of isopropylacetate to form a combined rich organic phase (~93 mL).

Thereafter the organic phase obtained as described above was combined with 45 mL of deoxygenated deionized water followed by removal of excess water (48 mL; pH ~1–2) which was sent to waste. The remaining reaction mixture contained the title product in ~90 mL of isopropyl acetate.

The reaction mixture produced as described above was combined with 150 mL of deoxygenated isopropyl acetate and thereafter subjected to azeotropic distillation (<95° C. to a KF<0.1 wt %) to provide a crude concentrated sample of the desired product. The crude product was cooled to 60–85° C. in 30 mL of heptane and seeded with 20 mg of crystals of the title product and held at that temperature for 1–2 hours. The process was repeated using a new batch of 30 mL of heptane.

The resulting product was cooled to 20–25° C. for 1–2 hours and filtered, washed with 60–90 mL of 3:2 heptane:isopropyl acetate and then vacuum dried at 50–55° C. to obtain 10.18 g of 82 Molar % of N-[(2S)-sulfanyl-4-(1,5,5-trimethylhydantoinyl) butanoyl]-L-leucyl-L-tert-leucine N-methylamide.

What is claimed is:

1. A method of producing N-[(2S)-thiobenzoyl-4-(1,5,5-trimethylhydantoinyl)butanoyl]-L-leucyl-L-tert-leucine N-methylamide comprising reacting 1,5,5-trimethyl-3-((3S)-thiobenzoyl-3-carboxypropyl)hydantoin and L-leucyl-L-tert-leucine N-methylamide with a base and an activating agent in the presence of an aprotic solvent and water.

2. The method of claim 1 wherein the base is selected from the group consisting of an alkali metal hydride, an alkaline earth metal hydride, an alkali metal hydroxide, an alkaline earth metal hydroxide, an alkoxide, and a tertiary amine.

3. The method of claim 1 wherein the base is a tertiary amine.

4. The method of claim 1 wherein the base is 4-methylmorpholine.

5. The method of claim 1 wherein the activating agent is selected from the group consisting of a haloformate; a thionyl halide; Vilsmeier reagent; a substituted carbodiimide; a substituted or unsubstituted phenyl carbodiimide optionally in the presence of hydroxybenzotriazole; chlorodimethoxytriazine; 4-(4,6-dimethoxy-1,3,5-triazin-2-yl)-4-methylmorpholinium halide; and an acid chloride.

6. The method of claim 1 wherein the activating agent is a haloformate.

7. The method of claim 1 wherein the activating agent is iso-butylchloroformate.

8. The method of claim 1 wherein the aprotic solvent is selected from the group consisting of an ether, an ester, an aromatic hydrocarbon, a halogenated aromatic hydrocarbon, a halogenated hydrocarbon and a nitrile.

9. The method of claim 1 wherein the aprotic solvent is an ester.

10. The method of claim 1 wherein the aprotic solvent is ethyl acetate.

11. The method of claim 1 wherein the amount of water is from about 0.1 to 5 molar equivalents relative to the amount of 1,5,5-trimethyl-3-((3S)-thiobenzoyl-3-carboxypropyl)hydantoin.

12. The method of claim 1 wherein the amount of water is about 1 molar equivalent relative to the amount of 1,5,5-trimethyl-3-((3S)-thiobenzoyl-3-carboxypropyl)hydantoin.

13. A method of forming N-[(2S)-sulfanyl-4-(1,5,5-trimethylhydantoinyl)butanoyl]-L-leucyl-L-tert-leucine N-methylamide comprising the steps of:

a) reacting 1,5,5-trimethyl-3-((3S)-thiobenzoyl-3-carboxypropyl)hydantoin and L-leucyl-L-tert-leucine N-methylamide with a base and an activating agent in the presence of an aprotic solvent and water to form N-[(2S)-thiobenzoyl-4-(1,5,5-trimethylhydantoinyl) butanoyl]-L-leucyl-L-tert-leucine N-methylamide; and b) reacting N-[(2S)-thiobenzoyl-4-(1,5,5-trimethylhydantoinyl)butanoyl]-L-leucyl-L-tert-leucine N-methylamide with a debenzoylating agent to produce N-[(2S)-sulfanyl-4-(1,5,5-trimethylhydantoinyl)butanoyl]-L-leucyl-L-tert-leucine N-methylamide.

14. The method of claim 13 wherein the base is selected from the group consisting of an alkali metal hydride, an alkaline earth metal hydride, an alkali metal hydroxide, an alkaline earth metal hydroxide, an alkoxide, and a tertiary amine.

15. The method of claim 13 wherein the base is a tertiary amine.

16. The method of claim 13 wherein the base is 4-methylmorpholine.

17. The method of claim 13 wherein the activating agent is selected from the group consisting of a haloformate; a thionyl halide; Vilsmeier reagent; a substituted carbodiimide; a substituted or unsubstituted phenyl carbodiimide optionally in the presence of hydroxybenzotriazole; chlorodimethoxytriazine; 4-(4,6-dimethoxy-1,3,5-triazin-2-yl)-4-methylmorpholinium halide; and an acid chloride.

18. The method of claim 13 wherein the activating agent is a haloformate.

19. The method of claim 13 wherein the activating agent is iso-butylchloroformate.

20. The method of claim 13 wherein the aprotic solvent is selected from the group consisting of an ether, an ester, an aromatic hydrocarbon, a halogenated aromatic hydrocarbon, a halogenated hydrocarbon and a nitrile.

21. The method of claim 13 wherein the aprotic solvent is an ester.

22. The method of claim 13 wherein the aprotic solvent is ethyl acetate.

23. The method of claim 13 wherein the amount of water is from about 0.1 to 5 molar equivalents relative to the amount of 1,5,5-trimethyl-3-((3S)-thiobenzoyl-3-carboxypropyl)hydantoin.

24. The method of claim 13 wherein the amount of water is about 1 molar equivalent relative to the amount of 1,5,5-trimethyl-3-((3S)-thiobenzoyl-3-carboxypropyl)hydantoin.

25. The method of claim 13 wherein the debenzoylating agent is selected from the group consisting of an alkali metal hydroxide, an alkaline earth metal hydroxide, an alkali metal alkoxide, ammonia, a primary amine, a secondary amine, an alkali metal thioalkoxide, a mineral acid, and an organic acid.

26. The method of claim 13 wherein the debenzoylating agent is a primary amine.

27. The method of claim 13 wherein the debenzoylating agent is 3-dimethylaminopropylamine.

* * * * *